(12) United States Patent
Agueci (10) Patent No.: US 9,044,217 B2
(45) Date of Patent: Jun. 2, 2015

(54) DISTRACTOR DEVICE FOR JOINTS

(75) Inventor: Alberto Agueci, Treviso TV (IT)

(73) Assignees: Alberto Agueci, Treviso TV (IT); ITALORTHOPEDICS S.A.S. DI INTERMEDIAZIONI COMMERCIALI S.R.L., Agrate Brianza MB (IT); ORTHOLAB S.R.L., Milan MI (IT)

( * ) Notice: Subject to any disclaimer, the term of this patent is extended or adjusted under 35 U.S.C. 154(b) by 795 days.

(21) Appl. No.: 13/387,046

(22) PCT Filed: Jul. 22, 2010

(86) PCT No.: PCT/EP2010/060656
§ 371 (c)(1),
(2), (4) Date: Apr. 5, 2012

(87) PCT Pub. No.: WO2011/012533
PCT Pub. Date: Feb. 3, 2011

(65) Prior Publication Data
US 2012/0191100 A1    Jul. 26, 2012

(30) Foreign Application Priority Data
Jul. 28, 2009    (IT) .............................. MI2009A1342

(51) Int. Cl.
*A61B 17/02* (2006.01)
*A61F 2/46* (2006.01)
*A61B 17/15* (2006.01)

(52) U.S. Cl.
CPC ............. *A61B 17/025* (2013.01); *A61F 2/4657* (2013.01); *A61B 17/155* (2013.01); *A61B 2017/0268* (2013.01)

(58) Field of Classification Search
CPC ............... A61B 17/025; A61B 17/155; A61B 2017/0268; A61F 2/4657
See application file for complete search history.

(56) References Cited

U.S. PATENT DOCUMENTS

| 2004/0122441 A1 | 6/2004 | Muratsu |
| 2004/0153084 A1 | 8/2004 | Haney et al. |
| 2008/0051798 A1 | 2/2008 | Colquhoun et al. |

FOREIGN PATENT DOCUMENTS

| EP | 0 327 249 A2 | 8/1989 |
| EP | 0 809 969 A2 | 12/1997 |

(Continued)

*Primary Examiner* — Christian Sevilla
(74) *Attorney, Agent, or Firm* — Lucas & Mercanti, LLP (57) ABSTRACT

A distractor device (1) comprises a distracting element that includes a fixed plate (3) and a mobile plate (4), said mobile plate (4) being translatable by means of an actuator with respect to a body (2) of said distracting element between a first position where it is in contact with said fixed plate (3) and a second position where it is spaced therefrom. The distractor device further includes at least one rod (10) suitable to be introduced in the medullary cavity of a femur (F) and provided with a stem (10a) and an abutment plate (10b) fixed at one end of the stem (10a) and inclined by a known angle (α) with respect thereto, said abutment plate (10b) being suitable to receive in abutment the mobile plate (4) in said second position, and one between the mobile plate (4) and the fixed plate (3) being also rotatable with respect to the other, the angle of rotation of the rotatable plate (3, 4) determined by the contact between the mobile plate (4) and the abutment plate (10b) being measured by means of a graduated scale (5d) and an indicator (4a) secured to said rotatable plate (3, 4). Thanks to these features, the distractor device according to the invention allows to check in situ and to correct the theoretical valgism angle of a patient's knee determined during a pre-surgery phase, thus allowing to correctly place the jig for the first distal resection of the femur.

10 Claims, 5 Drawing Sheets

(56) References Cited

FOREIGN PATENT DOCUMENTS

| WO | 98/25526 A1 | 6/1998 | | |
| WO | WO 9825526 A1 * | 6/1998 | ............. | A61B 17/15 |
| WO | 99/35972 A1 | 7/1999 | | |
| WO | WO 9935972 A1 * | 7/1999 | ............. | A61B 17/02 |

* cited by examiner

DISTRACTOR DEVICE FOR JOINTS

CROSS-REFERENCE TO RELATED APPLICATIONS

This application is a 371 of PCT/EP2010/060656, filed Jul. 22, 2010, which claims the benefit of Italian Patent Application No. MI2009A001342, filed Jul. 28, 2009, the contents of each of which are incorporated herein by reference.

FIELD OF THE INVENTION

The present invention relates to a distractor device for joints and in particular to a distractor device for the arthroplasty of the knee.

BACKGROUND OF THE INVENTION

Arthroplasty is a surgical operation wherein the damaged portions of a joint, such as the knee, are partially or completely replaced with special prostheses made of metal and plastic.

One of the most important aims of knee arthroplasty operations is to restore the original extension of the patient's leg by ensuring that the leg bones are correctly positioned with respect to each other and that the tension of the ligaments on both sides of the knee is balanced. Mistakes in restoring the original anatomic relationships may result in excessive stresses on the knee, which lead to an early failure of the arthroplasty.

The mechanical axis of the leg is an imaginary line on a frontal plane which connects the head of the femur with the center of the ankle and indicates the direction of the load supported by the leg of a person. In a healthy person the mechanical axis of the leg passes through the center of the knee, which ensures that the femoral condyles withstand the same load. In an injured patient the mechanical axis of the leg passes laterally to the center of the knee, thus concentrating a larger part of the load on one of the femoral condyles, which is consequently damaged.

The surface of the knee is enclosed on each side by the collateral ligaments, which in a healthy patient are equally tensioned when the leg is in the extended position. This tension of the lateral ligaments avoids lateral movements of the femur with respect to the tibia, also called varus/valgus movements. In an injured patient the femur and the tibia are not correctly positioned with respect to each other, which causes the mechanical axis of the leg to be bent thus causing a stretch of the collateral ligament located on the convex side of the deformation and a contraction of the collateral ligament located on the concave side.

In order to recover the anatomic functionality of a deformed knee, it is simultaneously required to lengthen the contracted collateral ligament, to tension both collateral ligaments so as to correctly counteract the varus/valgus movements when the leg is extended, and to verify that the mechanical axis of the leg passes through the center of the knee.

To this purpose, the facing ends of the femur and tibia are resected in order to remove their worn out portions and to make room for the components of a prosthesis suitable to correctly restore the anatomic relationships of the joint.

There are known distractor devices for knee arthroplasty that are inserted between the tibia and the femur when the leg is extended in order to move them away from each other, thus temporarily restoring the anatomic relationships of the joint, i.e. the correct position of the mechanical axis of the leg with respect to the knee and the balancing of the tension state of the collateral ligaments. Under these conditions, the surgeon can correctly define the resection levels of the ends of the tibia and femur in order to install the prostheses.

Knee distractor devices for arthroplasty are disclosed e.g. in U.S. Pat. No. 4,501,266 and EP 1915951 and in patent publications WO 98/25526, EP 809969, U.S. 2004/153084 and WO 99/35972.

The resections of the tibia and femur are made by using special slotted jigs which must be fixed on the respective bone by suitable pins. The correct positioning of the jigs in the longitudinal direction of the bone and their orientation with respect thereto are fundamental for a successful arthroplasty and it is therefore necessary to fix suitable reference points.

In the case of the tibia, the resection jig is typically mounted on a telescopic rod that is anchored to the ankle at one end and arranged along the longitudinal direction of the bone by taking the second finger of the foot as a reference. The rod so arranged is aligned with the mechanical axis of the leg. Once the alignment has been carried out, a clamping device is used, which allows the surgeon to correctly position the jig with respect to the end of the tibia in order to resect the desired bone portion. Once the positioning has been carried out, the jig is fixed on the tibia through relevant pins and the telescopic rod and the clamping device are removed in order to make room for the resection tools. The flat surface resulting from the resection is perpendicular to the mechanical axis of the leg.

In the case of the femur the procedure is more complex. In fact, in order to fix the prosthesis it is necessary to carry out multiple resections at the distal end, the first and most important of which must be made transversally to the femur by taking into account the valgism angle of the patient, while the others, generally four, are made on different planes by taking the plane of the first resection as a reference.

The valgism angle is measured during a pre-surgery phase with the help of a radiography of the patient's leg and it represents the angle between the mechanical axis of the leg and the anatomic axis of the femur, the latter passing through its medullary cavity. In a healthy person this angle is comprised between three and eight degrees.

In order to make the distal resections of the femur, it is known to initially bend the leg at 90° in order to drill the femur coaxially to the medullary cavity. A rod suitable to serve as a support for an instrument allowing to mount a first resection jig and to orient it according to the valgism angle measured during the pre-surgery phase is then inserted into the medullary cavity. As in the case of the tibia, the size of the bone portion to be resected is defined with the help of a clamping device connectable to the rod inserted in the medullary cavity of the femur.

Once the first resection has been carried out, the flat surface resulting therefrom is used as a base for placing a second instrument, which allows to fix the mounting pins of a second resection jig provided with four seats. The subsequent resections on the distal end of the femur are then carried out in a direction that is approximately perpendicular to the first one. Also in this phase it is necessary to precisely establish the orientation of the jig with respect to the bone, in particular, considering the plane of the first resection, its rotation angle around the rod inserted in the medullary cavity, in order to avoid mistakes in the resection of the femoral condyles that might lead to a wrong positioning of the prosthesis.

In order to improve the positioning of the surgical instruments used in knee arthroplasty many solutions have been developed.

U.S. 2004/0122441 discloses an apparatus for arthroplasty operations suitable for measuring a joint gap and ligament balance between an osteotomized surface at a femoral distal end and an osteotomized surface at a tibial proximal end. The apparatus is provided with a fixed plate extending from a body and suitable to contact the osteotomized surface at the tibial proximal end. The apparatus further comprises a vertically movable arm connected to the body at the free end of which a supporting plate is rotatably mounted. The supporting plate is so configured to contact the osteotomized surface at the femoral distal end.

EP 327249 discloses a modular apparatus for use in the preparation of bone surfaces and the implantation of a modular total knee prosthesis in a patient. The apparatus comprises resection guides, templates, alignment devices, a distractor and clamping instruments which provide modularity and facilitate bone resection and prosthesis implantation. During the surgical operation, the distractor is fixed to the femur by means of an alignment fork integral with a rod previously fitted into the medullary cavity. Subsequently, alignment devices are mounted on the distractor so fixed in order to determine suitable reference points for the pins supporting the resection jigs.

U.S. 2008/051798 discloses an alternative method for locating the mechanical axis of a long bone, which avoids the use of an intra-medullary rod. The method involves generating an image of the long bone and determining the angle between the mechanical axis of the bone and a reference axis. The method is implemented with a distractor assembly comprising a fixed plate and a mobile plate wherein the mobile plate is translatable by means of an actuator with respect to a body of the distractor assembly between a first position where it is in contact with the fixed plate and a second position where it is spaced therefrom. The mobile plate is also rotatable with respect to the fixed plate and the rotation angle is displayed by means of a graduated scale and an indicator.

In order to achieve a successful arthroplasty, the flat surfaces obtained by means of the resection of the tibia and of the first resection of the femur must result parallel to each other.

Since the rod diameter is lower than the diameter of the medullary cavity of the femur, once inserted into the medullary cavity the rod may be not correctly aligned with the anatomic axis of the femur. Starting from an unreliable reference system it is thus clear that the orientation of the first resection jig may be subject to even large variations with respect to what has been calculated during the pre-surgery phase, thus negatively affecting the restoring of the mechanical axis of the leg and the valgism angle once the prosthesis is installed.

Moreover, neither the known distractors nor the other known surgical tools used in arthroplasty procedures allow to check in situ the correctness of the calculations carried out during the pre-surgery phase on the valgism angle, which contributes to increase the risk of making mistakes when resecting the femur and of malfunction of the installed prosthesis.

EP 327249 in fact discloses a distractor device to be fixed to the femur by means of an intra-medullary rod provided with an engaging means in the form of a fork. The fork lies on a plane defining a specific angle with respect to the rod. Therefore, since the distractor is fixed to the fork, mistakes in the positioning of the rod with respect to the axis of the medullary cavity will lead to a wrong positioning of the distractor, the alignment devices and of resection masks.

On the other hand, U.S. 2008/051798 teaches the use of a graduated scale to allow the surgeon to find the correct position of the mechanical axis of the femur. However, the graduated scale is used in order to bring the femur in a position corresponding to a theoretical position determined pre-operatively. Therefore, mistakes in the pre-surgery calculations will result in a wrong positioning of the femur and consequently in a bad arthroplasty.

SUMMARY OF THE INVENTION

It is therefore an object of the present invention to provide a distractor device for arthroplasty allowing to overcome these disadvantages. Said object is achieved with a distractor device whose main features are disclosed in the first claim, while other features are disclosed in the remaining claims.

The distractor device for arthroplasty according to the present invention comprises a distracting element that includes a fixed plate and a mobile plate suitable to contact the tibia and the femur of a patient's leg, respectively. The device further includes at least one rod suitable to be introduced in the medullary cavity of the femur and provided with an abutment plate fixed at one end of the rod and inclined by a known angle with respect thereto. The abutment plate is suitable to receive in abutment the mobile plate of the distracting element and one between the mobile plate and the fixed plate is also rotatable with respect to the other one so that the mobile plate may completely contact the abutment plate. The rotation angle of the rotatable plate determined by the contact between the mobile plate and the abutment plate is measurable by means of a graduated scale and an indicator restrained to the rotatable plate.

The main advantage offered by the invention is that, thanks to the combined use of an abutment plate arranged at the end of the rod inserted in the medullary cavity and of a rotatable plate associated with a measuring system of the rotation angle, it is possible to precisely establish the position of the jig for the first distal resection of the femur by previously checking in situ the correspondence to the valgism angle determined during the pre-surgery phase, thus being able to modify the reference system before definitively fixing the resection jig.

Moreover, still thanks to the presence of a system for measuring the rotation angle of the rotatable plate, the distractor device according to the invention can be used also after the first distal resection of the femur in order verify the actual parallelism between the resections made on the tibia and femur, thus allowing to evaluate possible other corrective actions during the surgery before carrying out the further resections with the second resection jig.

Another advantage offered by the invention is that the distractor device has an extremely simple and inexpensive structure, so configured as to be easily adapted to the standard resection jigs used for knee arthroplasty.

BRIEF DESCRIPTION OF THE DRAWINGS

Further advantages and features of the distractor device according to the present invention will become clear to those skilled in the art from the following detailed and non-limiting description of an embodiment thereof with reference to the attached drawings, wherein.

DETAILED DESCRIPTION OF THE INVENTION

Figure 1:
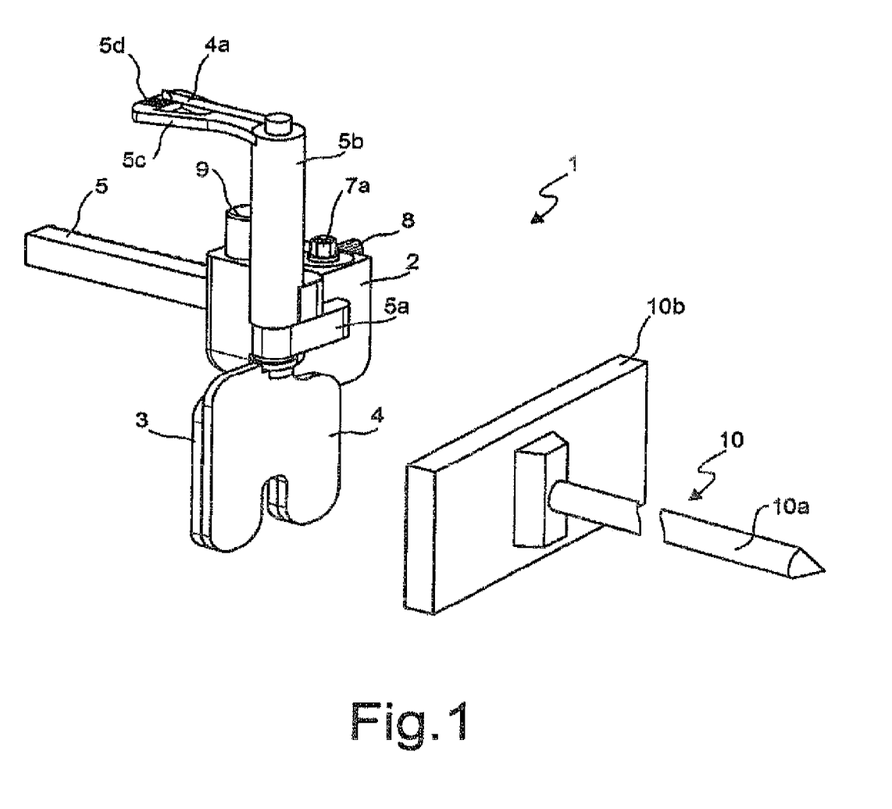
FIG. 1 is a perspective assembly view of a distractor device according to the invention.
Figure 2:
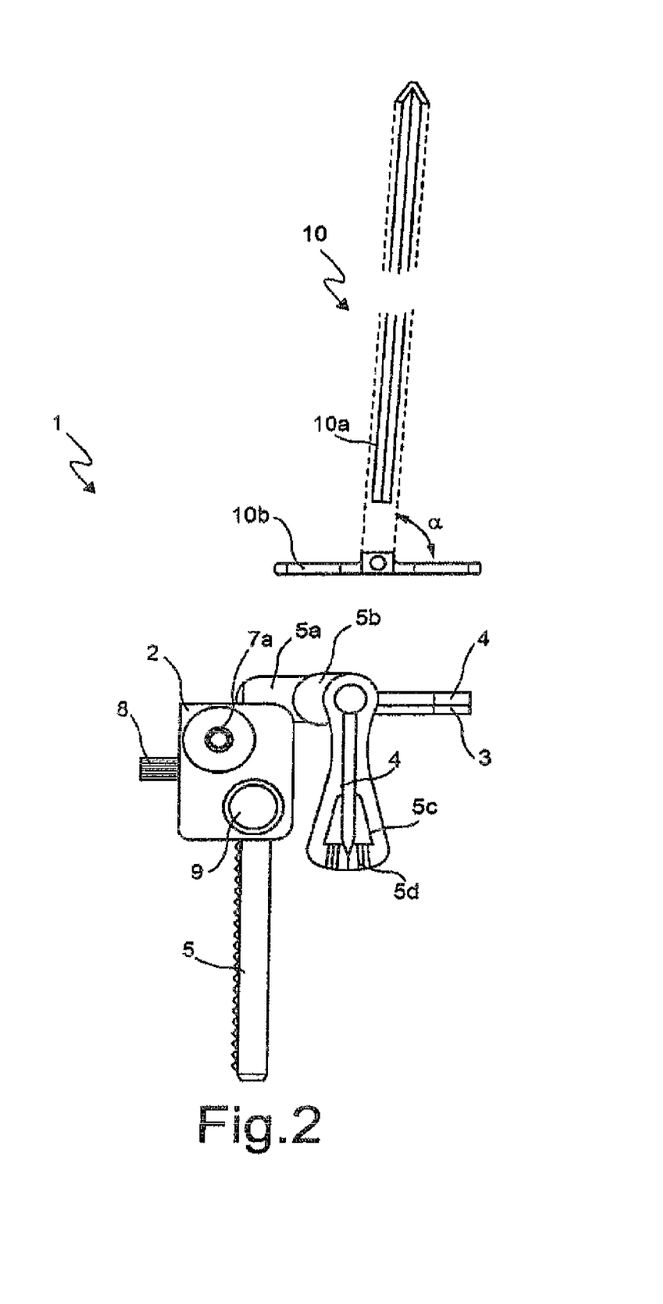
FIG. 2 is a top view of the device of FIG. 1.
Figure 3:
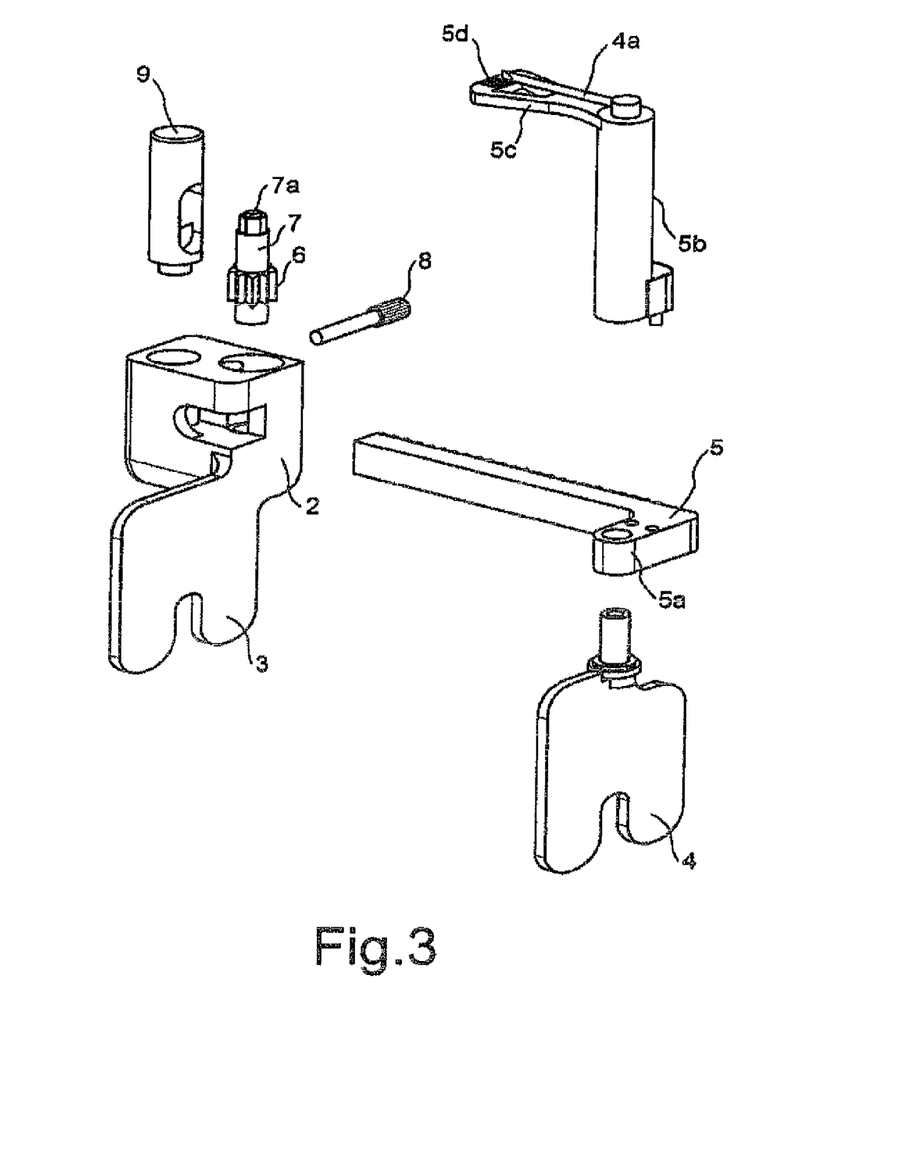
FIG. 3 is an exploded perspective view of the distracting element of the device of FIG. 1.

Referring to FIGS. 1, 2 and 3, the distractor device 1 according to the invention comprises in a known way a distracting element that includes a fixed plate 3 and a mobile plate 4. The mobile plate 4 is translatable by means of an actuator with respect to a body 2 of the distracting element between a first position where it is in contact with the fixed plate 3 and a second position where it is spaced therefrom.

When the distractor device 1 is inserted in the knee, the fixed plate 3 is placed in contact with the tibia of the patient's leg and the mobile plate 4 is spaced away from the fixed plate 3 thus contacting the distal end of the femur in order to distract the joint.

In the embodiment shown in FIGS. 1 to 3, the actuator is in particular a linear actuator and comprises a toothed rack 5 at one end 5a of which the mobile plate 4 is restrained. The toothed rack 5 can be driven by a toothed wheel 6 mounted on a shaft 7 provided with an end portion 7a suitable to receive a drive wrench (not shown), e.g. a torque wrench. The translation movement of the toothed rack 5 may be prevented or allowed by respectively acting on suitable locking and unlocking members 8, 9 of the actuator inserted in body 2, thus allowing to steadily maintain or adjust the distance between the plates 3, 4. The toothed rack 5 may also be provided with a graduated scale (not shown) suitable to allow to measure the distance between the fixed and mobile plates 3, 4.

According to the inventive concept underlying the invention, the distractor device 1 further comprises at least one rod 10 suitable to be introduced into the medullary cavity of a femur and provided with a stem 10a and an abutment plate 10b fixed at one end of stem 10a and inclined by a known angle α with respect thereto. When stem 10a is completely inserted in the medullary cavity of the femur, the abutment plate 10b abuts on the distal end of the femur and, in particular, on its condyles.

Moreover, one between the fixed plate 3 and the mobile plate 4 is rotatable with respect to the other, whereby when rod 10 of the distractor device is inserted in the medullary cavity of the femur the mobile plate 4 will contact the abutment plate 10b thus causing the rotation of the rotatable plate 3 or 4 until complete alignment of the flat surfaces of the mobile plate 4 and of the abutment plate 10b is achieved.

In the embodiment shown in FIGS. 1 to 3, the rotatable plate is the mobile plate 4, which is pivoted at the end 5a of the toothed rack 5. A hollow cylindrical body 5b is also restrained to the toothed rack 5 and a plate 5c carrying a graduated scale 5d indicating angle variations comprised in a predefined range, e.g. between −9° and +9°, is arranged on the top of the body 5b.

The angle of rotation of the rotatable plate 4 is displayed on the graduated scale 5d by means of a needle 4a rotationally restrained to the rotatable plate 4 through a shaft (not shown) arranged in the hollow cylindrical body 5b.

The angle α in rod 10 indicates a possible valgism angle of a patient's leg, stem 10a representing the anatomic axis of the femur and the abutment plate 10b representing a surface perpendicular to the mechanical axis of the leg.

Figure 4:
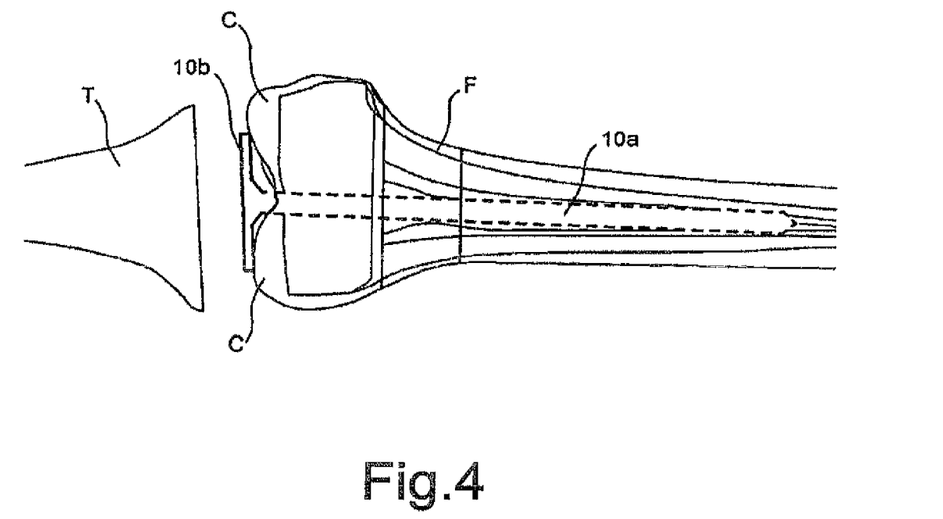
FIG. 4 is a schematic top view of the rod of the device of FIG. 1 inserted in the medullary cavity of the femur.

During an arthroplasty operation, in order to completely exploit the advantages of the device according to the invention the surgeon must first of all carry out in a known way a resection of the tibia perpendicularly to the mechanical axis of the leg. Once this operation is finished, the surgeon bends the leg by 90°, axially drills the femur in correspondence to the medullary cavity and then introduces rod 10 therein. As shown in FIG. 4, rod 10 is inserted into the medullary cavity of femur F until the abutment plate 10b abuts onto the condyles C.

Figure 5:
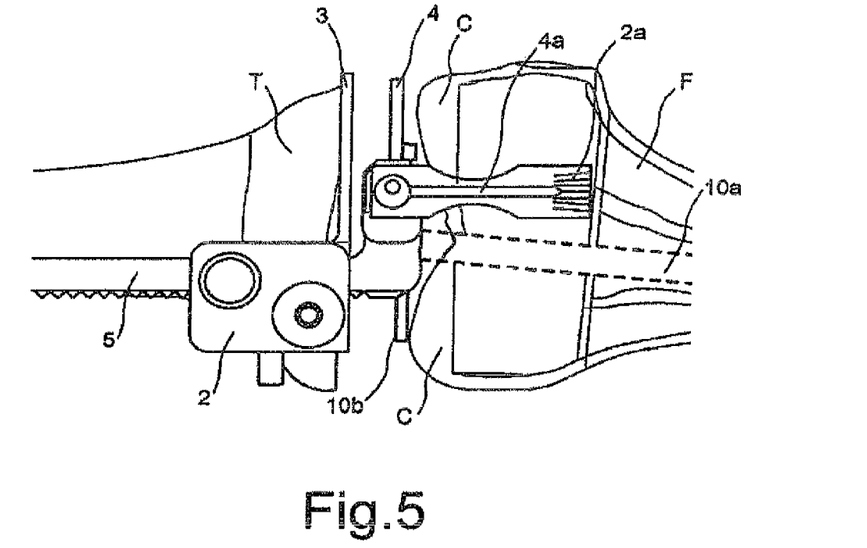
FIG. 5 is a top plan view showing the distractor device of FIG. 1 inserted between the tibia and the femur.

Subsequently, as shown in FIG. 5, the surgeon brings the patient's leg back in an extended position and places body 2 of distractor 1 on tibia T while inserting plates 3 and 4 between tibia T and femur F. In particular, the fixed plate 3 is arranged in contact with the flat surface previously obtained by resecting tibia T. The fixed plate 3 is thus aligned perpendicularly to the mechanical axis of the patient's leg.

By operating actuator 5, the mobile plate 4 is brought in abutment onto the abutment plate 10b and rotates until complete alignment of the respective flat surfaces is achieved. As it is known, in this phase tibia T and femur F are spaced away from one another in order to tension the collateral ligaments of the knee. The tensioning degree of the collateral ligaments may be controlled by using e.g. a torque wrench. On the basis of what has been discussed above, the rotatable plate rotates according to the angle α of rod 10 inserted in the medullary cavity of the femur.

The surgeon then reads the graduated scale 5d. According to the constraints system so obtained, if the theoretical valgism angle α of rod 10 corresponds to the real valgism angle of the knee, the value read on the graduated scale will be proximate to zero, i.e. plate 10b of rod 10 will be substantially parallel to the flat surface obtained by resecting tibia T. Otherwise, the surgeon will read a value other than zero and equal to the difference between the theoretical valgism angle calculated during the pre-surgery phase and the real angle determined by rod 10. In this case the surgeon will have to extract rod 10 and replace it with another rod 10 having a different angle α' corresponding to the previous one plus or minus the reading of the graduated scale. If also the new rod 10 leads to a reading other than zero, the surgeon will have to choose a further rod 10 having an angle α" and so on up to achieving a reading proximate to zero. Moreover, thanks to the possibility of measuring in real time and in situ the difference between the theoretical valgism angle and the real one, the surgeon can also carry out possible lyses of the ligaments necessary to correctly restore the anatomic relationships of the knee.

Figure 6:
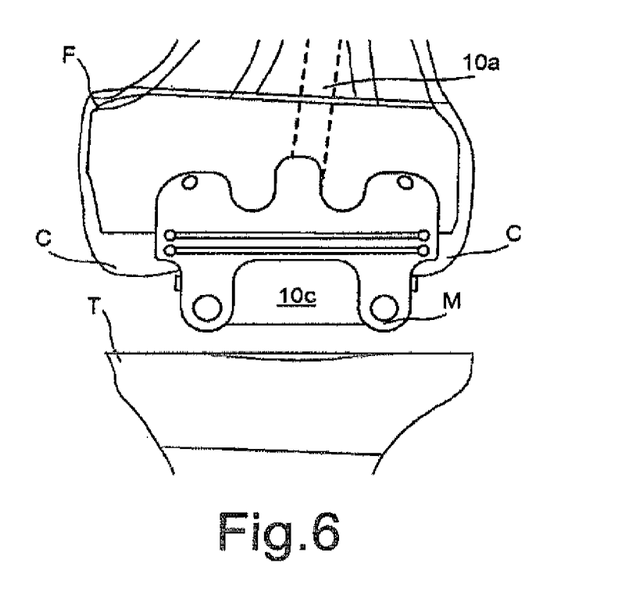
FIG. 6 is a top view showing the first resection jig of the femur mounted on the rod of the distractor device.

As shown in FIG. 6, once chosen the rod 10 most suitable for the surgery, the distracting element is removed from the knee and a supporting member 10c suitable to allow to mount a standard jig M for the distal resection of femur F is fixed on the abutment plate 10b. As it may be seen, jig M has a plurality of through-openings having the shape of slots and arranged parallel to the abutment plate 10b, thus allowing to carry out resections parallel to the resection already made on tibia T. The choice of the slot determines the amount of bone tissue that will be removed.

Figure 7:
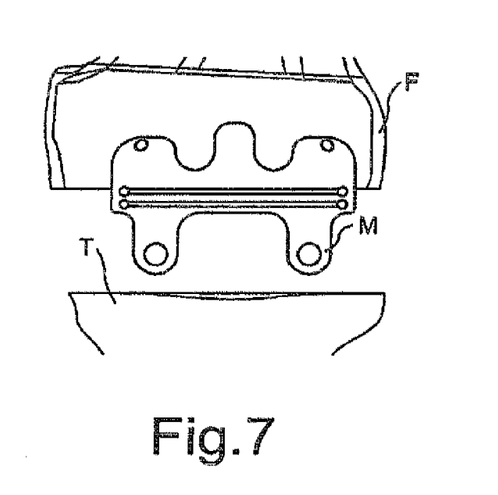
FIGS. 7 and 8 are top views showing the femur after the first distal resection with and without the first jig.
Figure 8:
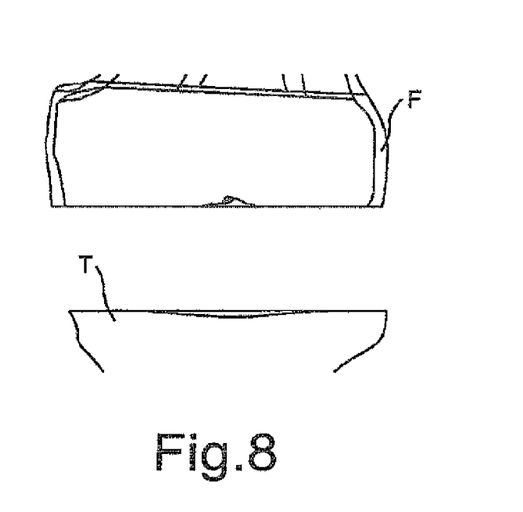

In order to carry out the resection the surgeon fixes jig M to femur F by means of suitable pins (not shown) and then removes the supporting member 10c from jig M and withdraws rod 10 from the medullary cavity of femur F, thus clearing the zone underneath jig M. FIGS. 7 and 8 respectively show the resected femur F with and without jig M.

Once the resection has been carried out, the surgeon can position the distracting element on tibia T again, inserting plates 3 and 4 between the flat surfaces of tibia T and femur F, in order to check the actual parallelism of the resections before proceeding to the subsequent steps of the surgery.

It is clear that the embodiment of the invention herein described and illustrated is just an example susceptible of numerous variants. For example, it is possible to provide a plurality of supporting members 10c to be mounted on the abutment plate 10b and configured so as to receive the different types of standard resection jigs used for knee arthroplasty.

Moreover, when the rotatable plate is the fixed plate 3, this will be pivoted on body 2 and the cylindrical body 5b, on the top of which plate 5c bearing the graduated scale 5d is arranged, will be restrained to body 2.

The invention claimed is:

1. Distractor device comprising a distracting element that includes a fixed plate and a mobile plate, said mobile plate being translatable by means of an actuator with respect to a body of said distracting element between a first position where the mobile plate is in contact with said fixed plate and a second position where the mobile plate is spaced from the fixed plate, one of the mobile plate and the fixed plate being also rotatable with respect to the other and an angle of rotation of the rotatable plate being measured by means of a graduated scale and an indicator secured to said rotatable plate, the device further comprising at least one rod provided with a stem suitable to be introduced in a medullary cavity of a femur (F), wherein said rod is provided with an abutment plate fixed at one end of said stem and inclined by a known angle ($\alpha$) with respect to the stem, said abutment plate being suitable to receive in abutment the mobile plate in said second position, said angle of rotation of the rotatable plate being determined by the contact between the mobile plate and the abutment plate.

2. Device according to claim 1, wherein the rotatable plate is the mobile plate.

3. Device according to claim 1, wherein the mobile plate is pivoted on the actuator.

4. Device according to claim 2, wherein said actuator is a linear actuator comprising a toothed rack that can be driven by a toothed wheel, said toothed wheel being mounted on a shaft provided with an end portion suitable to receive a drive wrench.

5. Device according to claim 1, wherein on the toothed rack there is rigidly secured a hollow cylindrical body carrying at a top a plate bearing a graduated scale suitable to indicate angle variations within a preset range.

6. Device according to claim 1, wherein said graduated scale has a measuring range between −9° and +9°.

7. Device according to claim 4, wherein the toothed rack is provided with a graduated scale suitable to allow a measurement of the distance between the fixed and mobile plates.

8. Device according to claim 1, wherein said indicator is a needle rotationally restrained to the rotatable plate.

9. Device according to claim 1, further comprising locking and unlocking members inserted in the body of the distracting element and suitable to prevent or allow a movement of the actuator.

10. Device according to claim 1, further comprising one or more supporting elements connectable to the abutment plate to allow a mounting of jigs (M) for the distal resection of the femur (F).

* * * * *